United States Patent
Gutierrez

[19]

[11] Patent Number: 6,161,556
[45] Date of Patent: Dec. 19, 2000

[54] DENTAL FLOSS HOLDER

[76] Inventor: Gregorio Gutierrez, 2462 18th Ave., Sacramento, Calif. 95820

[21] Appl. No.: 09/451,749

[22] Filed: Nov. 30, 1999

[51] Int. Cl.[7] .................................................. A61C 15/00
[52] U.S. Cl. ........................................... 132/327; 132/324
[58] Field of Search .................................... 132/327, 323, 132/324, 325, 326

[56] References Cited

U.S. PATENT DOCUMENTS

| | | | |
|---|---|---|---|
| 1,916,653 | 7/1933 | Bodde | 132/326 |
| 2,187,442 | 1/1940 | Beach | 132/326 |
| 3,814,114 | 6/1974 | Roberts | 132/326 |
| 4,832,062 | 5/1989 | Grollimund et al. | 132/327 |
| 5,094,256 | 3/1992 | Barth | 132/322 |
| 5,105,840 | 4/1992 | Giacopuzzi | 132/325 |
| 5,197,498 | 3/1993 | Stewart | 132/325 |
| 5,301,698 | 4/1994 | Ballard | 132/325 |
| 5,538,023 | 7/1996 | Oczkowski et al. | 132/323 |
| 5,573,021 | 11/1996 | Grofcisk et al. | 132/324 |
| 5,819,769 | 10/1998 | Gutiewez | 132/327 |

*Primary Examiner*—John J. Wilson
*Assistant Examiner*—Robyn Kieu Doan
*Attorney, Agent, or Firm*—Thomas R. Lampe

[57] ABSTRACT

A dental floss holder includes two holder elements. One of the holder elements has a pivot post attached thereto and the other holder element has an opening through which the pivot post projects. A cap is threadedly engaged with the pivot post and cooperates with a projection on one of the holder elements to clamp dental floss in position. Guide surfaces are provided on the cap and projection to guide the floss to the pivot post.

13 Claims, 3 Drawing Sheets

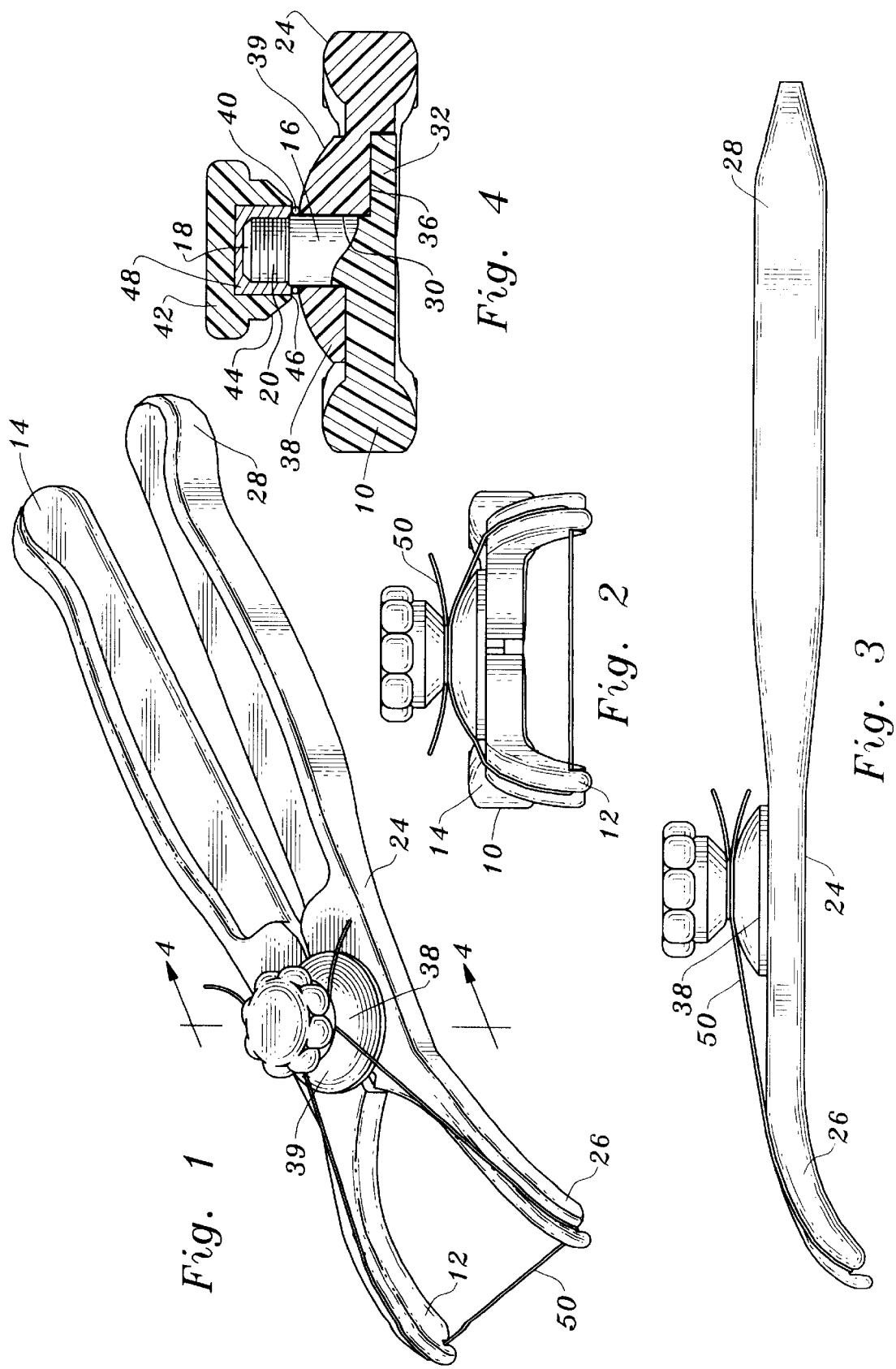

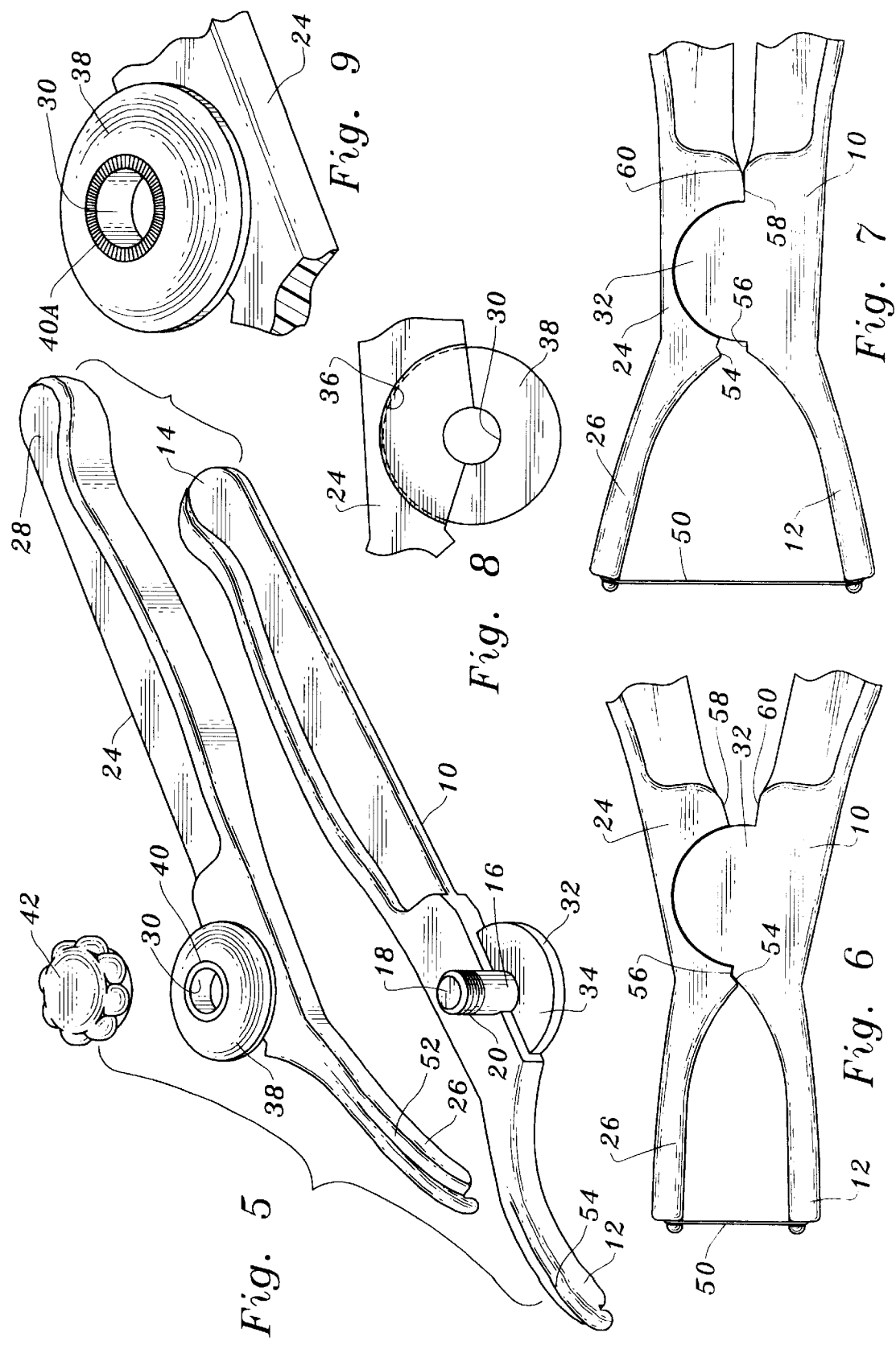

DENTAL FLOSS HOLDER

TECHNICAL FIELD

This invention relates to a dental floss holder used to hold and maneuver dental floss when flossing teeth.

BACKGROUND OF THE INVENTION

A great many devices have been conceived and developed for the purpose of holding dental floss during use. My U.S. Pat. No. 5,819,769, issued Oct. 13, 1998, discloses a dental floss system including a dental floss holder including two pivotal holder elements. Floss is positioned in slots formed at ends of the holder elements.

The following patents are cited to show floss holder mechanisms having a degree of pertinence to the invention disclosed and claimed herein: U.S. Pat. No. 5,105,840, issued Apr. 21, 1992, U.S. Pat. No. 4,832,062, issued May 23, 1989, U.S. Pat. No. 5,301,698, issued Apr. 12, 1994, U.S. Pat. No. 5,538,023, issued Jul. 23, 1996, U.S. Pat. No. 5,094,256, issued Mar. 10, 1992, U.S. Pat. No. 5,197,498, issued Mar. 30, 1993, and U.S. Pat. No. 5,573,021, issued Nov. 12, 1996.

DISCLOSURE OF INVENTION

The dental floss holder the present invention is characterized by its relative simplicity, low cost and ease of use, as compared with known floss holder arrangements. The dental floss holder incorporates a number of features which contribute to its functionality and convenience of operation.

The dental floss holder includes a double-ended, elongated first holder element including a floss-holding end and a manually graspable end.

A pivot post is attached to the first holder element between the floss holding end and manually graspable end thereof.

The pivot post projects away from the first holder element and has a distal end. The pivot post also has screw threads formed thereon along at least a portion of the length thereof.

The apparatus also includes a double-ended, elongated second holder element including a floss-holding end and a manually graspable end. The second holder element defines an opening between the floss-holding end thereof and the manually graspable end thereof.

The pivot post attached to the first holder element passes through the opening of the second holder element. The second holder element has a floss clamping surface adjacent to the opening.

The dental floss holder also includes a clamp member threadedly engaged with the pivot post at said screw threads and having a floss clamping surface. The clamp member is movable between a clamping position wherein the floss clamping surface of the second holder element and the floss clamping surface of the clamp member clampingly engage dental floss disposed about the pivot post and a non-clamping position wherein the floss clamping surface of the second holder element and the floss clamping surface of the clamp member do not clampingly engage the floss.

The second holder element is pivotal about the pivot post relative to the first holder element to selectively tighten or loosen a floss portion extending between the floss-holding ends of the first and second holder elements when the floss is clampingly engaged by the floss clamping surfaces.

Other features, advantages, and objects of the present invention will become apparent with reference to the following description and accompanying drawings.

BRIEF DESCRIPTION OF DRAWINGS

FIG. 1 is a perspective view of the dental floss holder of the present invention holding a length of floss;

FIG. 2 is a front, elevational view of the floss holder;

FIG. 3 is a right side view of the floss holder;

FIG. 4 is an enlarged sectional view taken along the line 4—4 in FIG. 1, and illustrating the pivot post of the holder partially sectioned;

FIG. 5 is an exploded perspective view illustrating the floss holder;

FIG. 6 is a bottom plan view illustrating floss-holding ends of the two holder elements of the device in one position;

FIG. 7 is a view similar to FIG. 6 but illustrating the floss-holding ends in another position;

FIG. 8 is an enlarged bottom plan view illustrating a portion of one of the holder elements;

FIG. 9 is a greatly enlarged perspective view illustrating a portion of an alternative embodiment of the dental floss holder.

MODES FOR CARRYING OUT THE INVENTION

Figure 10:
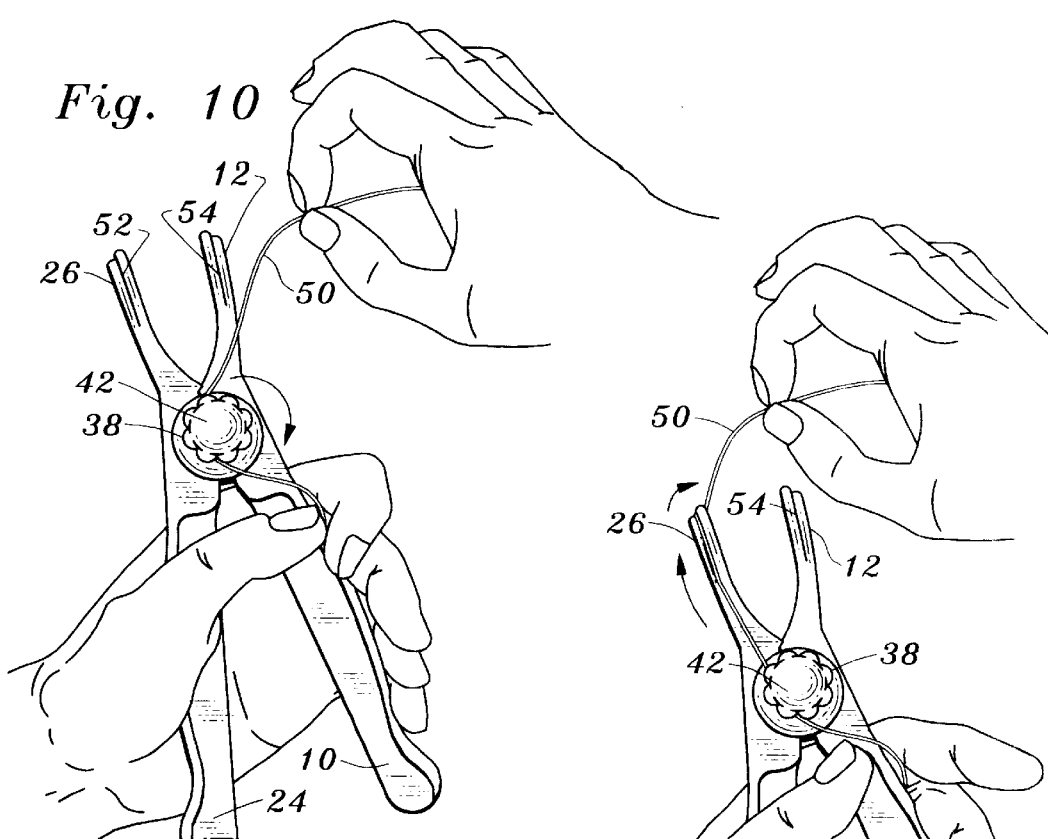
FIGS. 10–12 are perspective views of the floss holder illustrating application of floss to the holder in sequential steps.

Referring now to FIGS. 1–8 and 10–12, a dental floss holder constructed in accordance with the teachings of the present invention includes a double-ended, elongated holder element 10 including a floss-holding end 12 and a manually graspable end 14.

A pivot post 16 is attached to the holder element 10 between the floss holding end and the manually graspable end thereof. Pivot post 16 projects away from the holder element 10 and has a distal end 18. Screw threads 20 are formed on the pivot post.

A double-ended, elongated second holder element 24 is pivotally connected to the holder element 10. Holder element 24 includes a floss-holding end 26 and a manually graspable end 28. The holder element 24 defines an opening 30 between the floss-holding end thereof and the manually graspable end thereof. The pivot post 16 passes through the opening 30; thus the holder element 24 is rotatable about the pivot post relative to holder element 10. The distal end of the pivot post 16 is located a distance from the holder element 24, with the first holder element and the distal end of the pivot post positioned at opposed sides of the second holder element.

Holder element 10 includes a semi-circular stabilizing member 32 with a planar surface 34 from which pivot post 16 projects. The stabilizing member 32 is located in a recess 36 formed in holder element 24.

Holder element 24 includes a dome-like projection 38 about the opening 30. Projection 38 projects in the direction of the distal end of the pivot post. The dome-like projection has an outer peripheral projection surface 39 which diminishes in size in the direction of pivot post distal end 18. At the outermost end of the projection 38 an annular floss clamping surface 40 is formed. In the embodiment of FIGS. 1–8 and 10–12 the floss clamping surface 40 is smooth and flat. FIG. 9 illustrates an alternative embodiment wherein the floss clamping surface 40A is non-smooth, being in the form of a plurality of radially extending grooves.

A clamp member in the form of a internally threaded, manually rotatable cap 42 is threadedly engaged with pivot post 16 at the distal end thereof, cap 42 having an outer peripheral cap surface 44. Outer peripheral cap surface 44 terminates at a floss clamping surface 46 which is annular and flat and the surface 44 diminishes in size in the direction of the floss clamping surface. Surface 44 is tapered, being in the form of a truncated cone in the disclosed embodiment.

When the cap 42 is screwed down onto projection 38, the floss clamping surfaces of these two structural elements engage and will clamp into place any floss wrapped about the pivot post 16. When, however, the cap is unscrewed and moved to an unclamping position, the floss can be readily manually wound or unwound relative to the pivot post.

The surface 39 on projection 38 and the tapered surface 44 on the cap 42 provide a guide which will direct floss being wrapped about the pivot post toward the pivot post to facilitate winding. This, of course, is accomplished when the cap and projection are separated. The projection 38 also contributes to the process by resisting engagement between the fingertips of the user with the main portion of the holder element 24 from which projection 38 extends. That is, projection 38 elevates floss clamping surface 40 so the user's fingertips do not hit the flat surface of holder element 24 to which projection 38 is attached.

In the illustrated form of the dental floss holder shown in FIG. 4, the cap 42 includes an insert of brass or other metal 48 molded in situ within the outer portion of the cap, which may suitably be formed of plastic or the like. Alternatively, the cap may be of single piece construction with the threads being molded integrally during the cap injection molding process.

Installing or replacing floss in the dental floss holder is a very simple matter. This is, of course, accomplished when the cap 42 is partially unscrewed. Referring to FIG. 10, the user makes a wrap of the floss 50 clockwise about the pivot post and holds an end. Next, the floss is inserted into bifurcated end 26 of holder element 24. A floss retention channel 52 is formed adjacent to the bifurcated end to assist in threading the floss and maintaining it in place.

Figure 11:
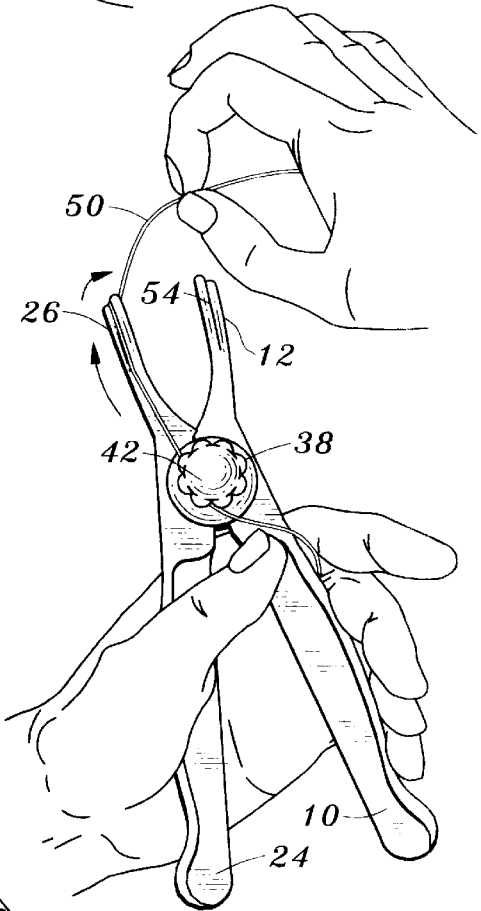

The floss 50 is then positioned in the bifurcated end 12 of holder element 10 as shown by the arrows in FIG. 11. Next, the floss is pulled downwardly with a portion thereof disposed in floss retention channel 54 located adjacent to floss-holding end 12.

Figure 12:
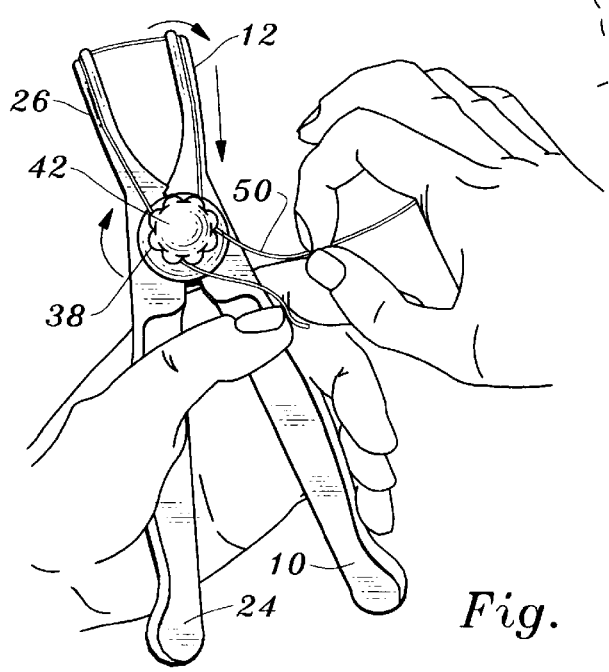

The second end of the floss is wrapped clockwise about pivot post 16 as shown in FIG. 12 and the cap 42 then screwed down to clamp the floss between floss clamping surface 46 and floss clamping surface 40.

The steps just described are carried out when the ends 12, 26 of the holder elements are relatively close together. FIG. 6 shows this configuration also. To maintain tension in that portion of the floss extending between the floss-holding ends, the user causes the manually graspable ends 14, 28 of the holder elements to move toward one another. This, of course, causes the floss-holding ends to move apart as shown in FIG. 7.

The dental floss holder includes abutment surfaces which limit relative movement of the holder elements between those configurations shown in FIGS. 6 and 7. These abutment surfaces are located adjacent to recess 36 and stabilizer member 32. With reference to FIG. 6 and 7, abutment surfaces 54, 56, located respectively on holder element 24 and holder element 10, come together when the holder elements have the relative positions shown in FIG. 6 to establish a minimum fixed distance between the floss-holding ends. Abutment surfaces 58, 60 formed respectively on holder elements 24 and 10 abut when the holder elements are in the relative positions shown in FIG. 7. This establishes a maximum fixed distance between the floss-holding ends.

What is claimed is:

1. A dental floss holder comprising, in combination:

a double-ended, elongated first holder element including a floss-holding end and a manually graspable end;

a pivot post attached to said first holder element between the floss holding end and manually graspable end thereof, said pivot post projecting away from said first holder element and having a distal end and having screw threads formed thereon along at least a portion of the length thereof;

a double-ended, elongated second holder element including a floss-holding end and a manually graspable end and defining an opening between the floss-holding end thereof and the manually graspable end thereof, said pivot post passing through said opening and said second holder element having a floss clamping surface adjacent to said opening; and a clamp member threadedly engaged with said pivot post at said screw threads and having a floss clamping surface, said clamp member movable relative to said second holder element and said pivot post when manually rotated about said pivot post to move axially along said pivot post between a clamping position wherein the floss clamping surface of said second holder element and the floss clamping surface of said clamp member clampingly engage dental floss disposed about said pivot post and a non-clamping position wherein the floss clamping surface of said second holder element and the floss clamping surface of said clamp member do not clampingly engage said floss, said second holder element being pivotal about said pivot post relative to said first holder element to selectively tighten or loosen a floss portion extending between the floss-holding ends of said first and second holder elements when the floss is clampingly engaged by said floss clamping surfaces, said clamp member having an outer peripheral clamp member surface diminishing in size in the direction of the floss clamping surface of said clamp member, said outer peripheral clamp member surface terminating at the floss clamping surface of said clamp member, said second holder element including a projection about said opening, the floss clamping surface of said second holder element located on said projection, said projection having an outer peripheral projection surface and a free end, the floss clamping surface of said second holder element located at said free end, and said outer peripheral projection surface diminishing in size in the direction of the floss clamping surface of the second holder element, said outer peripheral clamp member surface and said outer peripheral projection surface cooperable to guide floss being wound about said pivot post between the floss clamping surfaces.

2. The dental floss holder according to claim 1 wherein said outer peripheral clamp member surface is tapered.

3. The dental floss holder of claim 1 wherein said outer peripheral clamp member surface is in the form of a truncated cone.

4. The dental floss holder according to claim 1 wherein said outer peripheral projection surface has a dome-like configuration.

5. The dental floss holder according to claim 1 wherein said first holder element and said pivot post are integral with one another.

6. The dental floss holder according to claim 1 including movement limiting means for limiting pivotal movement between said first holder element and said second holder element.

7. The dental floss holder according to claim 6 wherein said movement limiting means comprises abutment surfaces on said first holder element and on said second holder element, abutment surfaces on said first holder element and said second holder element engageable when the floss-holding ends thereof are moving away from one another to establish a maximum fixed distance between said floss-holding ends.

8. The dental floss holder according to claim 6 wherein said movement limiting means comprises abutment surfaces on said first holder element and on said second holder element, abutment surfaces on said first holder element and said second holder element engageable when the floss-holding ends thereof are moving toward one another to establish a minimum fixed distance between said floss-holding ends.

9. The dental floss holder according to claim 6 wherein one of said holder elements defines a recess and wherein the other of said holder elements has a stabilizing member positioned in said recess and movable therein during pivotal movement between said holder elements, said movement limiting means being located adjacent to said recess and said stabilizing member.

10. The dental floss holder according to claim 1 wherein at least one of said floss clamping surfaces is non-smooth.

11. The dental floss holder according to claim 1 wherein said holder elements define floss retention channels extending from the floss holding ends thereof along portions of the lengths of said holder elements.

12. The dental floss holder according to claim 1 wherein the distal end of said pivot post is located a distance from said second holder element, with the first holder element and the distal end of the pivot post positioned at opposed sides of said second holder element.

13. The dental floss holder according to claim 9 wherein said second holder element defines said recess and wherein said first holder element is attached to said stabilizing member, said pivot post extending from said stabilizing member.

* * * * *